(12) United States Patent
Yoon (10) Patent No.: US 7,675,625 B2
(45) Date of Patent: Mar. 9, 2010

(54) APPARATUS FOR EXAMINING FLAT PANEL DISPLAY DEVICE AND EXAMINING METHOD THEREOF

(75) Inventor: Kyeung Sic Yoon, Gumi-si (KR)

(73) Assignee: LG. Display Co., Ltd., Seoul (KR)

( * ) Notice: Subject to any disclaimer, the term of this patent is extended or adjusted under 35 U.S.C. 154(b) by 582 days.

(21) Appl. No.: 11/479,757

(22) Filed: Jun. 29, 2006

(65) Prior Publication Data

US 2007/0152701 A1 Jul. 5, 2007

(30) Foreign Application Priority Data

Dec. 29, 2005 (KR) .................... 10-2005-0133993

(51) Int. Cl.
*G01N 21/55* (2006.01)
*G01N 21/00* (2006.01)

(52) U.S. Cl. .................... 356/445; 356/239.1; 356/432

(58) Field of Classification Search ................ 356/432, 356/445, 239.1
See application file for complete search history.

(56) References Cited

U.S. PATENT DOCUMENTS

| 5,691,811 | A | * | 11/1997 | Kihira | .................... 356/239.1 |
| 5,701,178 | A | * | 12/1997 | Burns et al. | ................ 356/600 |
| 5,870,204 | A | * | 2/1999 | Chiu et al. | .................. 356/430 |
| 6,275,286 | B1 | * | 8/2001 | Haubold et al. | .......... 356/239.1 |
| 6,362,884 | B1 | * | 3/2002 | Okahira et al. | .............. 356/399 |
| 6,570,651 | B1 | * | 5/2003 | Haubold et al. | .......... 356/239.1 |
| 6,671,041 | B2 | * | 12/2003 | Okahira et al. | ............ 356/237.1 |
| 6,707,546 | B2 | * | 3/2004 | Okahira et al. | ........... 356/239.1 |
| 6,930,772 | B2 | * | 8/2005 | Maezono et al. | ......... 356/239.1 |
| 7,077,019 | B2 | * | 7/2006 | Weiss et al. | ................ 73/865.8 |
| 7,369,240 | B1 | * | 5/2008 | Abbott et al. | ............... 356/429 |
| 7,382,457 | B2 | * | 6/2008 | Kiraly | ........................ 356/430 |
| 7,420,671 | B2 | * | 9/2008 | Sonda | ....................... 356/239.1 |
| 7,495,760 | B2 | * | 2/2009 | Miyake et al. | ........... 356/239.1 |
| 2004/0057046 | A1 | * | 3/2004 | Abbott et al. | ............... 356/239.1 |
| 2004/0179193 | A1 | * | 9/2004 | Maezono et al. | ......... 356/239.1 |
| 2006/0098190 | A1 | * | 5/2006 | Miyake et al. | ........... 356/239.1 |

* cited by examiner

*Primary Examiner*—Roy Punnoose
(74) *Attorney, Agent, or Firm*—Brinks Hofer Gilson & Lione (57) ABSTRACT

An apparatus for examining a flat panel display device and a method thereof is provided. The tact time for examining a glass substrate is reduced as much as possible, manufacturing costs are reduced by simplifying a product, and a foot print is reduced. The apparatus includes a base frame, a carrier carrying a glass substrate from a side to the opposite side of the base frame, an auto-probe to capture an image of the glass substrate and examining whether or not the glass substrate is inferior using captured data, and a visual inspector inclining the front side of the glass substrate forward to allow inspection of the glass substrate with the naked eye. According to the apparatus, the tact-time is shortened and the foot print is reduced.

17 Claims, 7 Drawing Sheets

APPARATUS FOR EXAMINING FLAT PANEL DISPLAY DEVICE AND EXAMINING METHOD THEREOF

This application claims the benefit of Korean Patent Application No. 10-2005-133993, filed on Dec. 29, 2005, which is hereby incorporated by reference as if fully set forth herein.

BACKGROUND OF THE INVENTION

1. Field of the Invention

The present invention relates to an apparatus for examining a glass substrate of a flat panel display device, and more particularly, to an apparatus for examining a flat panel display device in which the tact time for examining inferiority of the glass substrate is reduced as much as possible, manufacturing costs are reduced by simplifying a product, and a foot print is reduced, and an examining method thereof.

2. Discussion of the Related Art

Generally, a flat panel display device is a display device designed to reduce big volume and heavy weight, disadvantages of a cathode ray tube. Flat panel display devices, generally include a liquid crystal display, a field emission display, a plasma display panel, and a light emitting display.

The apparatus for examining the flat panel display devices as described above is designed to determine whether or not the flat panel display device is inferior such that a light is projected to the glass substrate (for example, an LCD panel) and a worker checks the quantity of the reflected light.

The apparatus for examining a flat panel display device includes a visual inspector for determining the inferiority by a worker's visual inspection and an auto-probe using a vision system.

In other words, by using the auto-probe, various inferiorities including the inferiorities difficult to detect with the naked eye are examined and the worker carries out the visual inspection using the visual inspector to determine whether or not the glass substrate is inferior.

In this case, inferiority includes a pixel inferiority with respect to a specific coordinate, a line inferiority of the specific coordinate, and a foreign matter inferiority.

However, in the conventional apparatus for examining a flat panel display device, since the auto-probe and the visual inspector are independently provided, the foot print of the processing line for examining is increased.

Additionally, since there is required a separate carrier for carrying the glass substrate from the auto-probe to the visual inspector (or from the visual inspector to the auto-probe), manufacturing costs are increased.

Moreover, since a procedure for examining the inferiority of the glass substrate must be sequentially carried out at two places, the working time, that is, the tact time is longer.

SUMMARY OF THE INVENTION

The present invention is directed to an apparatus for examining a flat panel display device and a examining method thereof that substantially obviate one or more problems of the related art.

An object of the present invention is to provide an apparatus for examining a flat panel display device in which a foot print of the oval apparatus is minimized, the tact time is reduced, and manufacturing costs are reduced, and an examining method of the flat panel display device using the same.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an apparatus for examining a flat panel display device includes a base frame for forming a body of the apparatus, a carrier installed along the upper side of the base frame to carry a glass substrate from a side of the base frame to the opposite side of the base frame, an auto-probe for capturing an image of the glass substrate carried by the carrier and examining whether or not the glass substrate is inferior using captured data, and a visual inspector installed on a side of the base frame to incline the front side of the glass substrate carried by the carrier forward and to inspect the glass substrate with the naked eye.

In another aspect of the present invention, an examining method using an apparatus for examining a flat panel display device includes providing a glass substrate to a side of a base frame; carrying the provided glass substrate to the opposite side of the base frame; capturing an image of the carried glass substrate with the auto-probe to determine the inferiority of the glass substrate; and previously erecting the glass substrate carried to the opposite side of the base frame at a predetermined angle and illuminating the glass substrate to inspect whether or not the glass substrate is inferior with the naked eye.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in FIGS. 1 to 7. Wherever possible, the same reference numbers will be used throughout the drawings to refer to the same or like parts, and additional descriptions for the same will be omitted.

Figure 1:
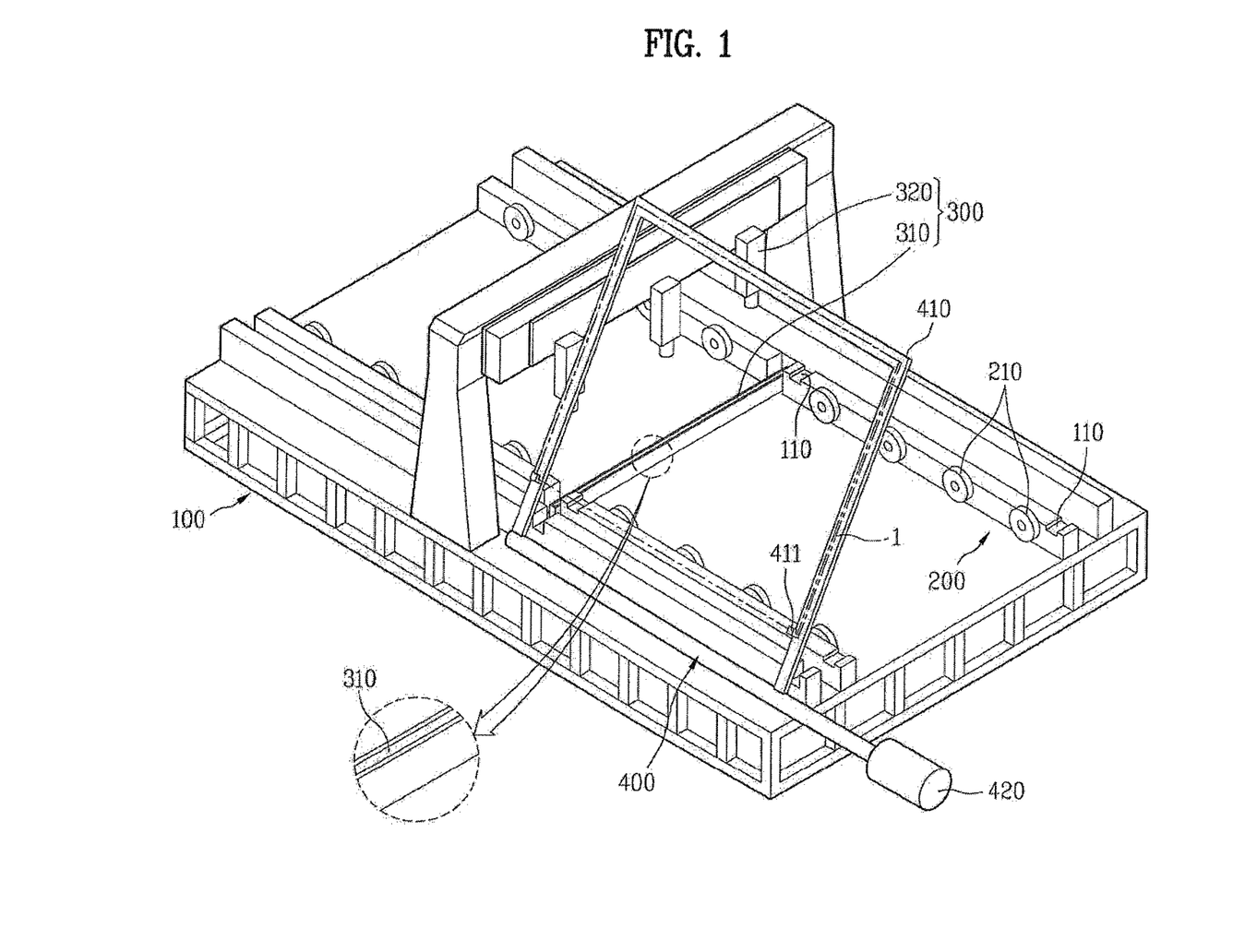
FIG. 1 is a perspective view illustrating an external appearance of an apparatus for examining a flat panel display device according to a first preferred embodiment of the present invention.
Figure 2:
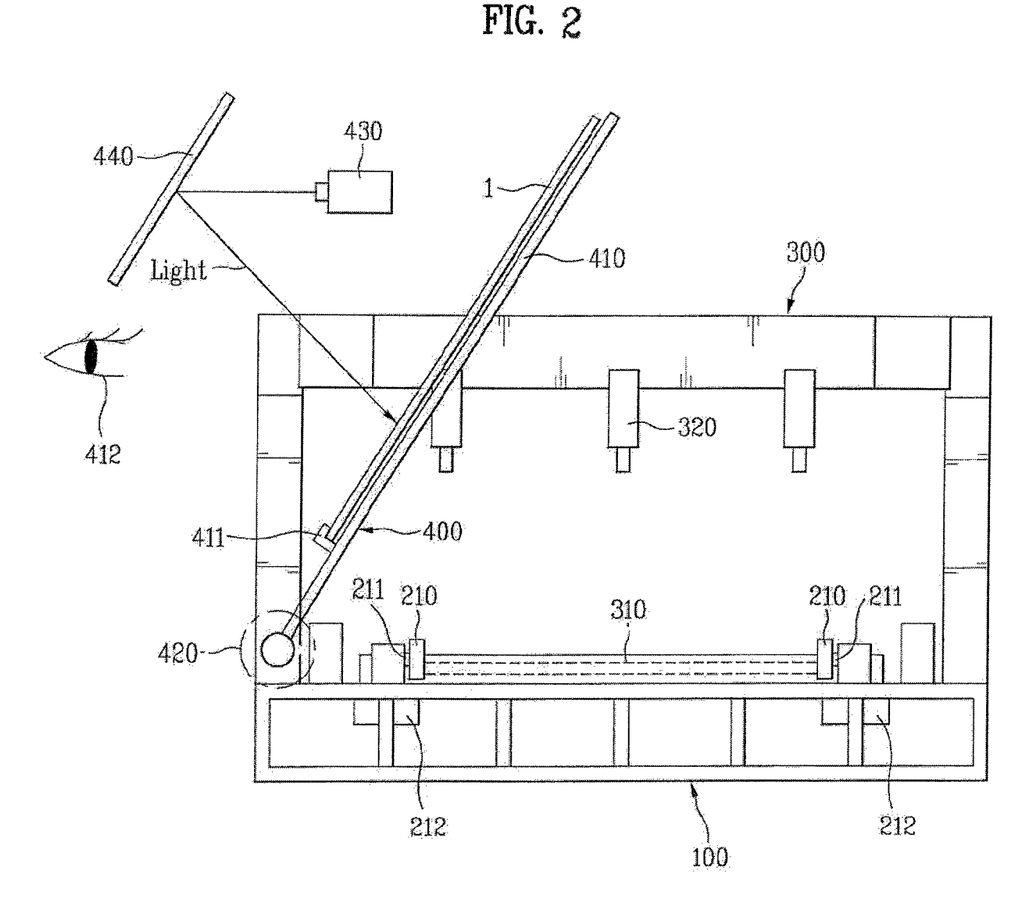
FIG. 2 is a side view illustrating the apparatus for examining a flat panel display device according to the first preferred embodiment of the present invention.

The accompanying drawings, FIGS. 1 and 2 illustrate the apparatus for examining a flat panel display device according to a first preferred embodiment of the present invention.

As shown in FIGS. 1 and 2, the apparatus for examining a flat panel display device according to the first preferred embodiment of the present invention includes a base frame 100, a carrier 200, an auto-probe 300, and a visual inspector 400.

The base frame 100 forms the body of the apparatus for examining a flat panel display device. The base frame 100 is formed lengthwise in the direction where the process progresses such that none of separate structures are around the upper inner side thereof. In other words, the base frame 100 is structured such that frames are positioned only in the front side (the left side in FIG. 1), the rear side, and the lateral sides, and the internal space is empty.

The carrier 200 is installed to move along the upper ends of the base frame 100 and is structured such that a glass substrate 1 is loaded on the upper side thereof, so that the carrier 200 carries the glass substrate 1 from a side of the base frame 100 to the opposite side thereof. The carrier 200 includes a plurality of rollers 210 installed to roll along the upper sides of the base frame 100 and a first driving unit 212 for driving the respective rollers 210.

In this case, shafts 211 of the respective rollers 210 may be made to receive driving force from the first driving unit 212 through belts (not shown) simultaneously, or may be respectively equipped with the first driving units.

The auto-probe 300 is a device for capturing an image of the glass substrate 1 carried by the carrier 200 and inspecting whether or not the glass substrate 1 is inferior using captured data of the glass substrate 1. The auto-probe 300 includes a first illumination unit 310, an image capture unit 320, and an inspection unit (not shown).

Particularly, the first illumination unit 310, as shown in FIG. 1, is installed on the upper sides (in the lower side in comparison to the respective roller) of the base frame 100 lengthwise in the forward-rearward direction to illuminate the lower surface of the glass substrate 1 passing over the first illumination unit 310.

In this case, the first illumination unit 310 preferably includes one of a fluorescent lamp with internal electrodes such as a cold fluorescent lamp (CFL) and a cold cathode fluorescent lamp (CCFL), an external electrode fluorescent lamp (EEFL) in which electrodes are provided outside of a tube, or a light emitting diode (LED).

The image capture unit 320 is a camera for capturing an image of the glass substrate 1. The image capture unit 320 is installed at a position on the upper space of the base frame 100 (at the upper side of the first illumination unit), corresponding to the position of the first illumination unit 310.

Although not depicted in the drawings, the first illumination unit 310 and the image capture unit 320 may be installed by exchanging their positions. In other words, it is possible that the first illumination unit 310 is installed in the upper side of the base frame 100 and the image capture unit 320 is installed in the lower side of the base frame 100.

The inspection unit is a device for analyzing data captured by the image capture unit 320 to determine the inferiority of the glass substrate 1.

Preferably, the inspection unit is implemented by a computer for receiving the data from the image capture unit 320 via wired line or wireless line and processing the data. The auto-probe 300 preferably includes a display (not shown) for allowing a worker to confirm the inferiority extracted by the inspection unit.

The visual inspector 400 is a device for inclining the glass substrate 1 carried by the carrier 200 such that the front side of the glass substrate is inclined forward so that the worker may inspect the glass substrate 1 with the naked eye 412.

The visual inspector 400 includes a loading frame 410, a second driving unit 420, and a second illumination unit 430. The loading frame 410 is formed in a rectangular shape having only a rim for supporting the circumferential lower side of the glass substrate 1 and an open inside. The front end of the loading frame 410 is preferably provided with a gripper 411 bent from the front end thereof to support a front end of the glass substrate 1.

The loading frame 410 is preferably sunken into the upper inside of the base frame 100.

Portions of the upper surface of the base frame 100 on which the loading frame 410 is placed are respectively formed with recesses 110. The depth of the recesses 110 is preferably lower than the uppermost level of the respective rollers 210 of the carrier 200. In other words, the loading frame is disposed below the surface on which the glass substrate is carried. This is for preventing the loading frame 410 from interfering with the carrying of the glass substrate 1 during the auto-probing with respect to the glass substrate 1.

The second driving unit 420 is a device driven to incline the loading frame 410 forward. The second driving unit 420 includes a motor having a shaft coupled with the front end of the loading frame 410.

The second illumination unit 430, as shown in FIG. 2, is installed in the upper space of the portion where the loading frame 410 is positioned.

Particularly, the visual inspector 400 of the first preferred embodiment of the present invention, as shown in FIG. 2, further includes at least one reflective plate 440 for reflecting a light provided from the second illumination unit 430 to the glass substrate 1.

Hereinafter, a method of examining the glass substrate 1 using the apparatus for examining a flat panel display device according to the first preferred embodiment of the present invention will be described with reference to the accompanying drawings, FIGS. 1 to 4, as follows.

After the glass substrate 1 is carried from the side (the opposite side where the visual inspector is installed) of the base frame 100, the carried glass substrate 1 is loaded on the upper sides of the respective rollers 210 of the carrier 200.

In this state, when the first driving unit (not shown) is driven, the respective roller 210 roll and the glass substrate 1 is moved to the opposite side (where the visual inspector is installed) of the base frame 100.

Figure 3:
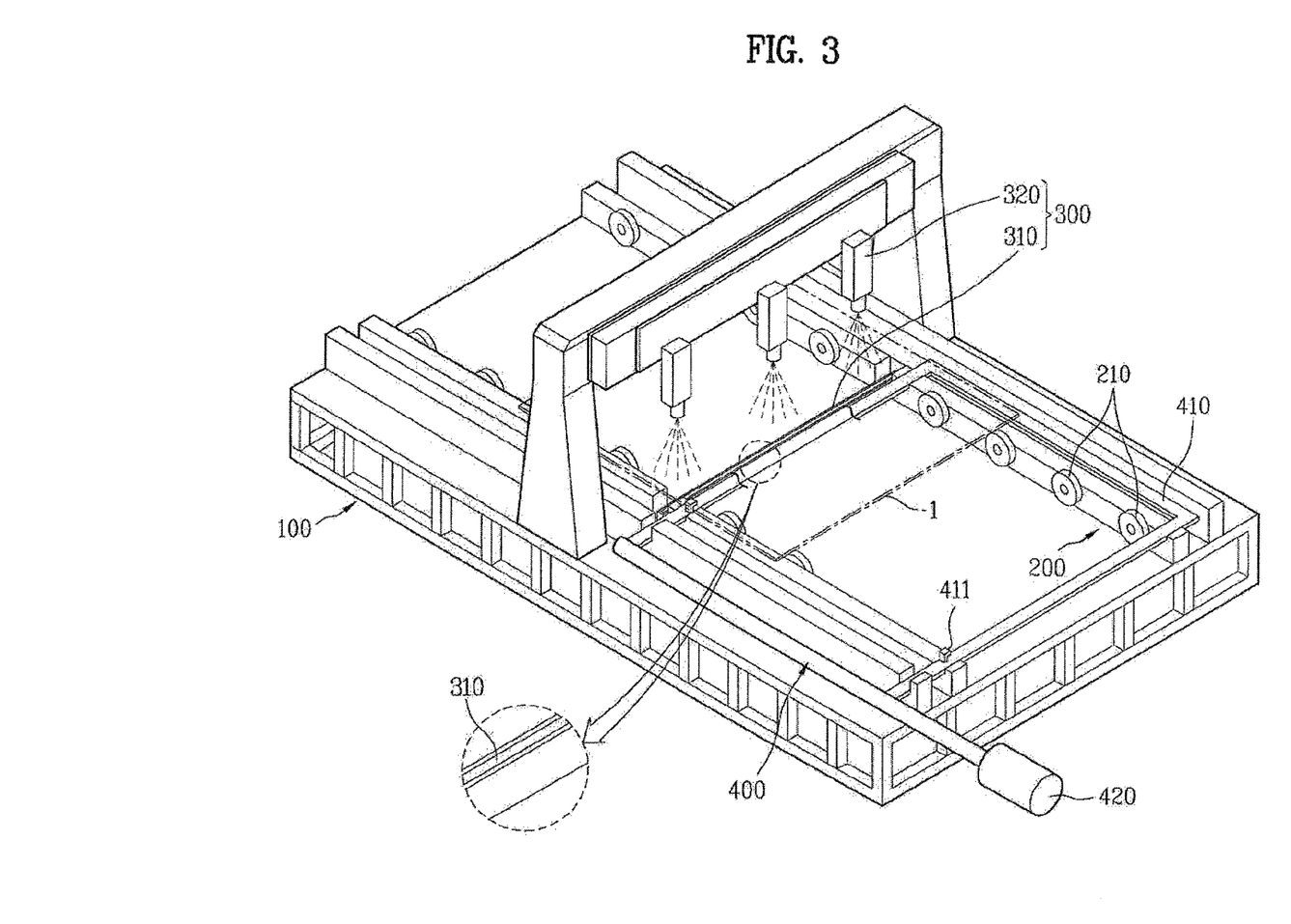
FIGS. 3 and 4 are operational views illustrating an inferiority examining procedure of a glass substrate carried out by the apparatus for examining a flat panel display device according to the first preferred embodiment of the present invention.

As shown in FIG. 3 the first illumination unit 310 of the auto-probe 300 illuminates the lower surface of the glass substrate 1 and the image capture unit 320 of the auto-probe 300 continuously captures images of the glass substrate 1 and scans the glass substrate 1.

The data captured by the image capture unit 320 is used by the inspection unit (not shown) in extracting the inferiority. The result information extracted is displayed on the display (not shown) so that the worker can confirm whether the glass substrate 1 is inferior or not.

Figure 4:
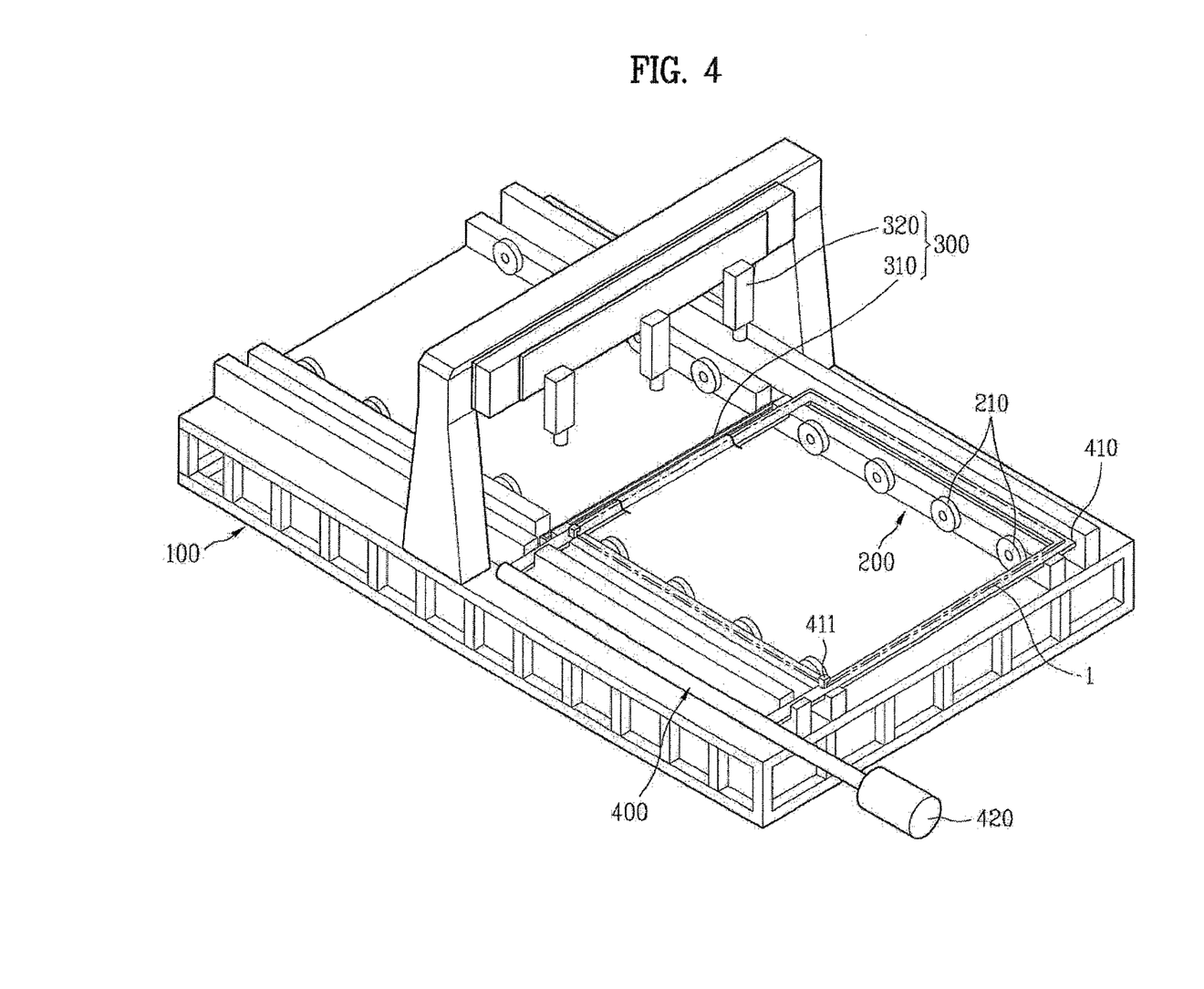

When the sequential auto-probing as described above is completed, the glass substrate 1 is positioned at the direct upper side of the loading frame 410 of the visual inspector 400, that is, the opposite side of the base frame 100 as illustrated in FIG. 4.

When the worker wishes to perform the visual inspection of the glass substrate 1 with the naked eye 412, the second driving unit 420 is driven and the loading frame 410 is gradually inclined upward. In other words, as shown in FIG. 1, the rear side of the loading frame 410 is gradually elevated about the portion of the loading frame 410 coupled with the second unit 420 through the shaft. At this time, since the front side of the glass substrate 1 is supported by the gripper 411 of the loading frame 410, the glass substrate 1 is prevented from sliding down in the inclined direction.

When the loading frame 410 is positioned at a predetermined angle, the second illumination unit 430 emits light, as shown in FIG. 2, to illuminate the upper surface (the front surface) of the glass substrate 1 loaded on the loading frame 410.

By doing so, the worker stands in front of the visual inspector 400 to inspect the glass substrate 1 with the naked eye 412 and determine whether or not the glass substrate 1 is inferior.

Due to the sequence described above, the auto-probing and the visual inspection of the glass substrate 1 are continuously carried out. Thus, the process time or tact time for examining the inferiority can be reduced.

Figure 5:
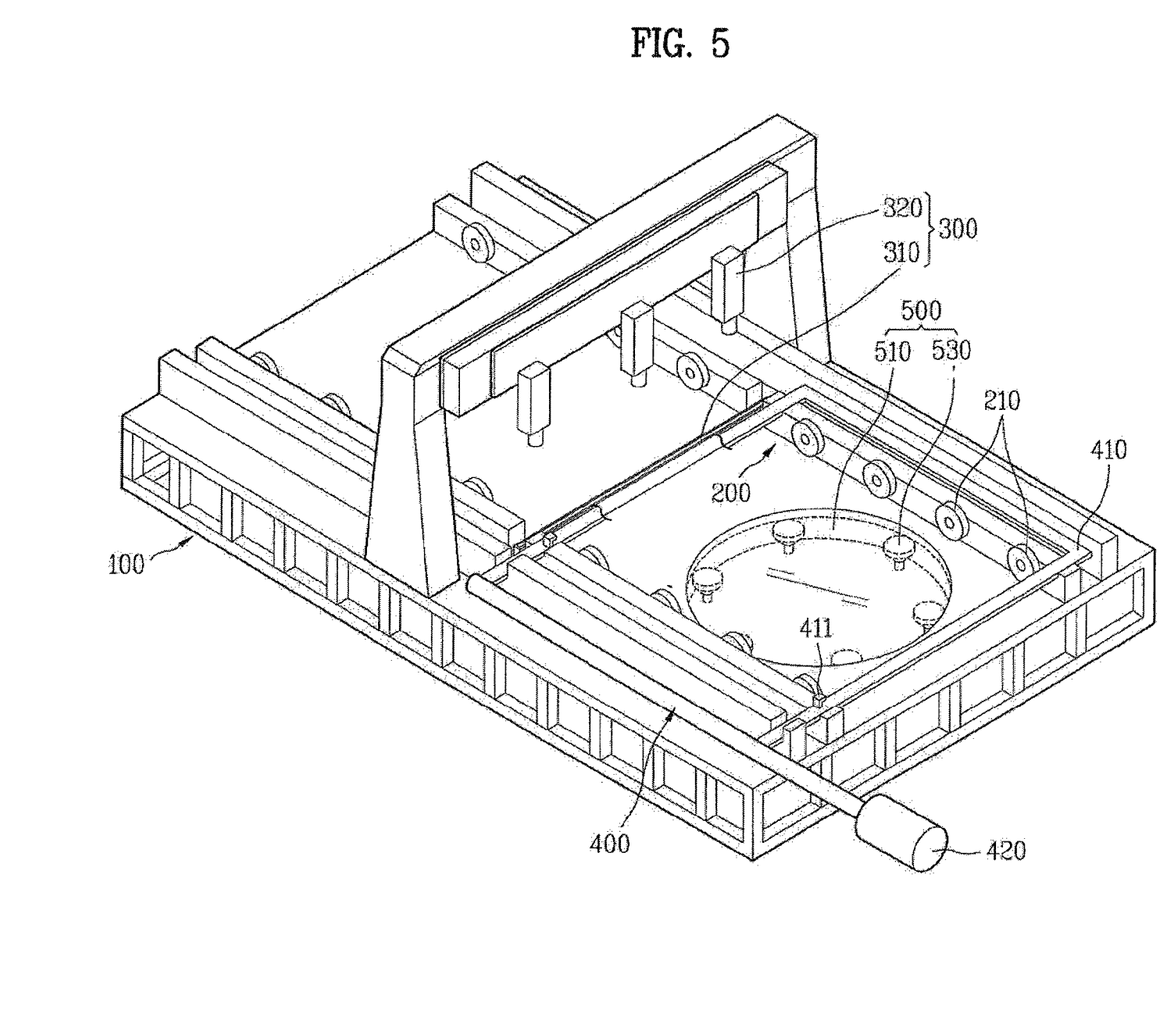
FIG. 5 is a perspective view illustrating an external appearance of an apparatus for examining a flat panel display device according to a second preferred embodiment of the present invention.

According to a second preferred embodiment of the present invention, FIG. 5 illustrates an apparatus for examining a flat panel display device. The apparatus for examining a flat panel display device according to the second preferred embodiment of the present invention further includes a reversing unit 500. The reversing unit 500 is a device for reversing the glass substrate 1 right or left. In other words, the auto-probing of the glass substrate 1 can be carried out in the state of reversing the glass substrate 1 by the reversing unit 500, so that the glass substrate 1 can be precisely examined as to whether the entire area of the glass substrate 1 is inferior or not.

Figure 6:
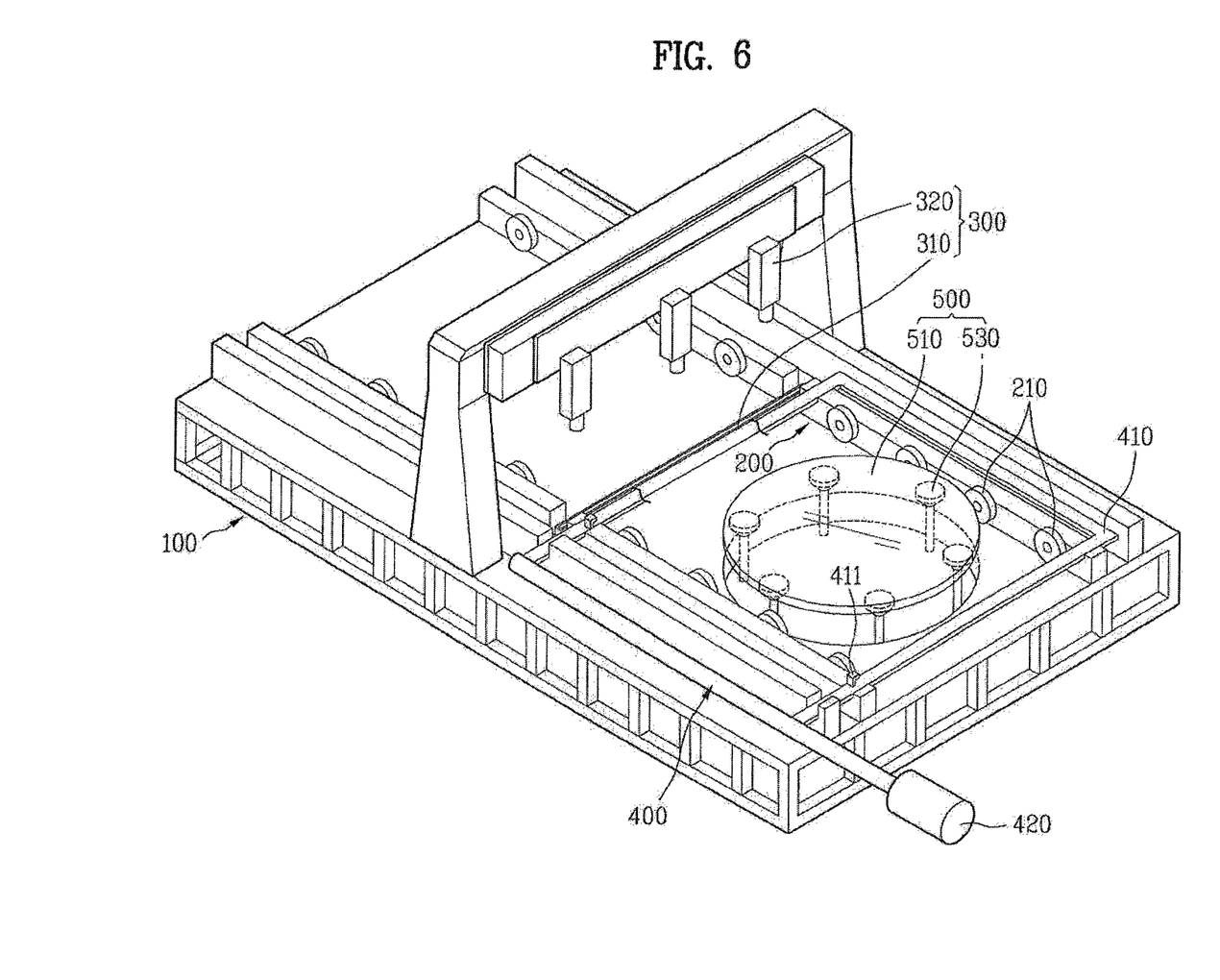
FIG. 6 is a perspective view illustrating operation of a reversing unit of the apparatus for examining a flat panel display device according to the second preferred embodiment of the present invention.

The reversing unit 500, as shown in FIGS. 5 and 6, includes a loading plate 510, a rotation unit (not shown), and an elevation unit 530. The glass substrate 1 is loaded onto the loading plate 510 which is formed as a circular plate. The rotation unit is a device driven to rotate the loading plate 510 and is installed at the inner lower side of the base frame 100.

The elevation unit 530 is a device driven to selectively elevate and lower the loading plate 510, and is coupled with an actuator (not shown) via a shaft. There is at least one elevation unit 530 and preferably multiple elevation units 530.

The reversing unit 500 of the apparatus for examining a flat panel display device according to the second preferred embodiment of the present invention will now be described in detail.

First, the glass substrate 1 is carried to the side where the visual inspector 400 is located and is loaded on the upper sides of the respective rollers 210.

The respective elevation units 530 elevate when the glass substrate is rotated left or right.

Accordingly, the loading plate 510 moves upward and the glass substrate 1 is separated from the upper sides of the rollers 210.

When the glass substrate 1 is separated from the upper sides of the respective rollers 210, the rotation unit is driven to rotate the loading plate 510, so that the glass substrate 1 is reversed to a desired position.

The respective elevation units 530 are then lowered down and the reversed glass substrate 1 is loaded on the upper sides of the respective rollers 210 again. The respective rollers 210 are then reversely driven and the reversed glass substrate 1 is carried to the side where the auto-probe 300 is positioned to carry out the inferiority examination.

Figure 7:
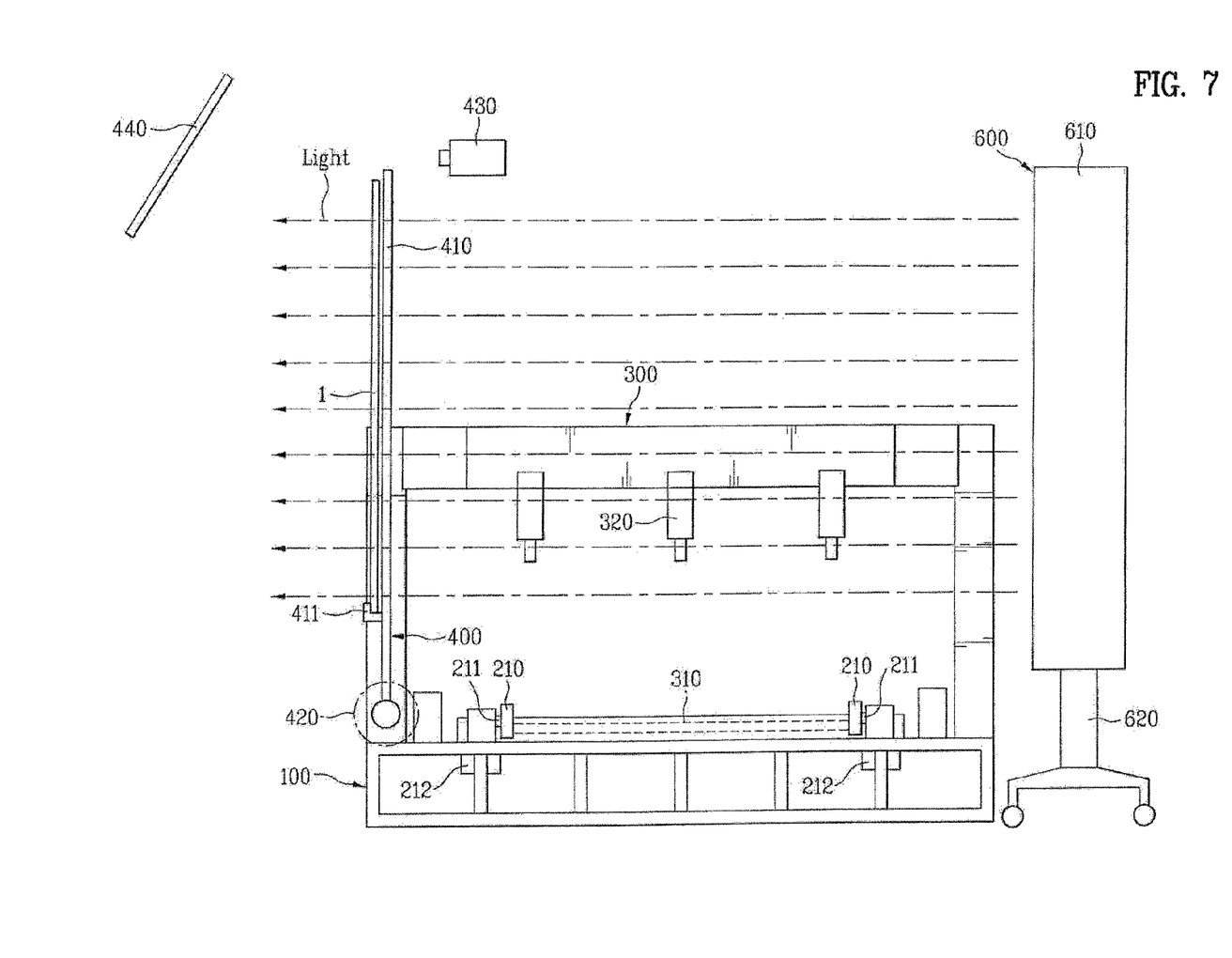
FIG. 7 is a side view illustrating an apparatus for examining a flat panel display device according to a third preferred embodiment of the present invention.

FIG. 7 illustrates an apparatus for examining a flat panel display device according to a third preferred embodiment of the present invention.

The apparatus for examining a flat panel display device according to the third preferred embodiment of the present invention further includes a transparent illumination unit 600. The transparent illumination unit 600 is a device installed in the rear side of a portion where the visual inspector 400 is positioned to illuminate the rear side of the glass substrate 1. In other words, the apparatus for examining a flat panel display device according to the third preferred embodiment of the present invention further includes the transparent illumination unit 600 which performs the inferiority examination of the glass substrate 1 using the transparent illumination.

In this case, the transparent illumination unit 600 includes at least one third illumination unit 610 for emitting light and a mounting frame 620 on which the third illumination unit 610 is installed.

A process of examining whether or not the glass substrate 1 is inferior using the apparatus for examining a flat panel display device according to the third preferred embodiment of the present invention will now be described in detail.

When the inferiority examination of the glass substrate 1 using the transparent illumination is performed, the second driving unit 420 is driven to rotate the loading frame 410 to be completely erected in the vertical direction as shown in FIG. 7.

The third illumination unit 610 of the transparent illumination unit 600 emits light to illuminate the rear surface of the glass substrate 1 loaded on the loading frame 410. Accordingly, the workers in front of the glass substrate 1 can inspect the glass substrate 1 with the naked eye.

The inferiority examination of the glass substrate 1 using the transparent illumination may be carried out prior to or after carrying out the inferiority examination of the glass substrate 1 using the reflective illumination provided in the first preferred embodiment of the present invention.

The apparatus for examining a flat panel display device according to the present invention can be modified in various manners in accordance with needs as described in the respective preferred embodiments.

As described above, the apparatuses for examining a flat panel display device according to the respective preferred embodiments of the present invention are structured such that the auto-probes are respectively integrally formed with the respective visual inspectors so that the foot print can be minimized.

Since there is no need for the separate visual inspector, no additional devices are required and manufacturing costs are minimized.

Further, since the auto-probing and the visual inspection of the glass substrate can be continuously carried out, the entire tact-time can be also reduced.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. An apparatus that examines a flat panel display device comprises:
   a base frame that forms a body of the apparatus;
   a carrier installed along the upper side of the base frame that carries a glass substrate of the flat panel display device from a side of the base frame to the opposite side of the base frame;
   an auto-probe that captures an image of the glass substrate carried by the carrier;
   a visual inspector installed on a side of the base frame to incline the front side of the glass substrate carried by the carrier forward and to inspect the glass substrate with the naked eye; and
   a reversing unit installed on the upper side of the base frame,
   wherein the visual inspector is installed on the upper side,
   wherein the reversing unit rotates the glass substrate carried to a desired position,
   wherein the reversing unit rotates the glass to a one direction of right and left directions.

2. The apparatus that examines a flat panel display device as set forth in claim 1, wherein the carrier comprises:
   a plurality of rollers that roll along the upper side of the base frame; and
   a first driving unit that drives the respective rollers.

3. The apparatus that examines a flat panel display device as set forth in claim 1, wherein the auto-probe comprises:
   a first illumination unit that illuminates the glass substrate;
   an image capture unit that captures an image of the glass substrate; and
   an inspection unit that analyzes the data captured by the image capture unit and extracts the inferiority of the glass substrate.

4. The apparatus that examines a flat panel display device as set forth in claim 3, wherein the first illumination unit is installed at the lower side of the base frame to illuminate the lower surface of the glass substrate; and
   the image capture unit is installed at a position of the upper side of the base frame corresponding to the position of the first illumination unit to capture an image of the glass substrate.

5. The apparatus that examines a flat panel display device as set forth in claim 1, wherein the visual inspector comprises:
   a loading frame on which the glass substrate is loaded;
   a second driving unit driven to incline the front side of the loading frame forward; and
   a second illumination unit that illuminates the glass substrate loaded on the loading frame.

6. The apparatus that examines a flat panel display device as set forth in claim 5, wherein the loading frame is sunken into the upper inside of the base frame such that the loading frame does not interfere with the carrying of the glass substrate during the auto-probing with respect to the glass substrate.

7. The apparatus that examines a flat panel display device as set forth in claim 6, wherein the loading frame is formed in the form of a rectangular frame having only rim and an open inside.

8. The apparatus that examines a flat panel display device as set forth in claim 5, wherein the second illumination unit is installed in the upper space of a portion where the loading frame is positioned.

9. The apparatus that examines a flat panel display device as set forth in claim 5, wherein the visual inspector further includes at least one reflective plate that reflects a light provided from the second illumination unit to the glass substrate.

10. The apparatus that examines a flat panel display device as set forth in claim 1, wherein the reversing unit comprises:
    a loading plate installed to rotate and be elevated to load the glass substrate thereon;
    a rotation unit driven to rotate the loading plate; and
    at least one elevation unit driven to elevate the loading plate.

11. The apparatus that examines a flat panel display device as set forth in claim 1, further comprising a transparent illumination unit installed in the rear side of a portion of respective portions of the base frame, where the visual inspector is positioned, to illuminate forward.

12. The apparatus that examines a flat panel display device as set forth in claim 11, wherein the transparent illumination unit comprises:
    at least one third illumination unit for emitting light; and
    a mounting frame in which the third illumination unit is installed.

13. An examining method using an apparatus that examines a flat panel display device comprising the steps of:
    (1) providing a glass substrate to a side of a base frame;
    (2) carrying the provided glass substrate to the opposite side of the base frame;
    (3) capturing an image of the carried glass substrate with the auto-probe;
    (4) previously erecting the glass substrate carried to the opposite side of the base frame at a predetermined angle and illuminating the glass substrate to inspect whether or not the glass substrate is inferior with the naked eye, and reversing the glass substrate to carry the glass substrate from the opposite side of the base frame to the side where the auto-probing is carried out such that the auto-probing is carried out again.

14. The examining method using an apparatus that examines a flat panel display device as set forth in claim 13, wherein the step (4) comprises the sub-step of (a) inclining the glass substrate at a predetermined angle and providing a reflective illumination to the front surface of the glass substrate to perform the inferiority examination of the glass substrate with the naked eye.

15. The examining method using an apparatus that examines a flat panel display device as set forth in claims 14, wherein the step (4) further comprises the sub-step of (b) providing a transparent illumination to the rear surface of the glass substrate after vertically erecting the glass substrate from the ground to perform the inferiority examination of the glass substrate with the naked eye.

16. The examining method using an apparatus that examines a flat panel display device as set forth in claim 15, wherein the sub-step (a) is carried out before the step (b).

17. The examining method using an apparatus that examines a flat panel display device as set forth in claim 15, wherein the sub-step (a) is carried out after the step (b).

* * * * *